(12) United States Patent
Hsiao

(10) Patent No.: US 10,413,630 B1
(45) Date of Patent: Sep. 17, 2019

(54) WALL SOCKET MOUNTED SOLID FRAGRANCE AROMA DIFFUSER

(71) Applicant: DONGGUAN YIH TEH ELECTRIC PRODUCTS CO., LTD., Dongguan (CN)

(72) Inventor: Ming Jen Hsiao, Miaoli County (TW)

(73) Assignee: DONGGUAN YIH TEH ELECTRIC PRODUCTS CO., LTD., Dongguan (CN)

(*) Notice: Subject to any disclaimer, the term of this patent is extended or adjusted under 35 U.S.C. 154(b) by 0 days.

(21) Appl. No.: 16/177,129

(22) Filed: Oct. 31, 2018

(51) Int. Cl.
*A61L 9/14* (2006.01)
*A61L 9/12* (2006.01)

(52) U.S. Cl.
CPC .................. *A61L 9/14* (2013.01); *A61L 9/122* (2013.01); *A61L 2209/12* (2013.01); *A61L 2209/15* (2013.01)

(58) Field of Classification Search
CPC ........ A61L 9/14; A61L 9/122; A61L 2209/12; A61L 2209/15
See application file for complete search history.

(56) References Cited

U.S. PATENT DOCUMENTS

| | | | |
|---|---|---|---|
| 7,963,460 B2 | 6/2011 | Hsiao | |
| 7,992,801 B2 | 8/2011 | Hsiao | |
| 8,029,153 B2 | 10/2011 | Hsiao | |
| 8,133,440 B2 | 3/2012 | Hsiao | |
| 8,196,903 B2 | 6/2012 | Hsiao | |
| 8,201,957 B2 | 6/2012 | Hsiao | |
| D708,312 S | 7/2014 | Hsiao | |
| 8,765,073 B1 * | 7/2014 | Hsiao | A61L 2/00 239/34 |
| 2007/0122306 A1 * | 5/2007 | Brown | A61L 9/122 422/5 |
| 2007/0207066 A1 * | 9/2007 | Thur | A61L 9/042 422/121 |
| 2014/0126892 A1 | 5/2014 | Hsiao | |

* cited by examiner

*Primary Examiner* — Sean E Conley
(74) *Attorney, Agent, or Firm* — Sinorica, LLC (57) ABSTRACT

A wall socket mounted solid fragrance aroma diffuser includes a bottom housing, an electrical plug assembly mounted in the bottom housing at one side, an air bearing seat mounted in the bottom housing, an air delivery device mounted inside the bottom housing and electrically coupled to the electrical plug assembly and adapted for creating a flow of air through the air bearing seat, and breathable fragrance capsules respectively filled with a solid fragrance material and placed in the air bearing seat in a stack. Each breathable fragrance capsule has vent holes on the opposing top and bottom sides for aroma diffusion so that the breathable fragrance capsule can be placed in the air bearing seat on either of the top and bottom sides, facilitating installation and replacement.

15 Claims, 8 Drawing Sheets

WALL SOCKET MOUNTED SOLID FRAGRANCE AROMA DIFFUSER

BACKGROUND OF THE INVENTION

1. Field of the Invention

The present invention relates to scent releasing devices and more specifically, to a wall socket mounted solid fragrance aroma diffuser.

2. Description of the Related Art

Aromatic air emitting devices that have excellent aroma volatilization effect and are safe and convenient to use are the products demanded by the market. The aroma of solid fragrance materials is not easy to volatilize, and their effect is not significant, so solid fragrance materials are often used in small spaces, such as drawers or wardrobes. USD708312 discloses a solid fragrance material entitled "Fragrance block set". U.S. patent application Ser. No. 13/669,402 discloses an aroma diffuser; however, the aroma diffusing ability of this design is weak, and it is difficult to have an optimal fragrance effect. Further, an aromatic substance heated by a heating element such as an electric resistance heating aroma is used to produce a fragrance. Similar design is seen in U.S. Pat. No. 8,201,957. However, using electric resistance to heat essential oil or fragrant wax must consider electric heating safety. Further, the use of a wall socket mounted aroma diffuser must overcome the limitation of wall socket mounting angle to prevent the fluid fragrance from being poured out.

SUMMARY OF THE INVENTION

The present invention has been accomplished under the circumstances in view. It is therefore an object of the present invention to provide a wall socket mounted solid fragrance aroma diffuser, which uses a breathable fragrance capsule filled with a solid fragrance material for diffusing a pleasant smell, wherein the solid fragrance material has open spaces therein so that a flow of air can be delivered through the open spaces in the solid fragrance material to agitate the solid fragrance material, thereby carrying the fragrance molecules to the outside open air in a safety manner.

It is another object of the present invention to provide a wall socket mounted solid fragrance aroma diffuser, which uses a breathable fragrance capsule filled with a solid fragrance material, wherein the breathable fragrance capsule has vent holes on the opposing top and bottom sides for aroma diffusion so that the breathable fragrance capsule can be placed in the diffuser on either of the top and bottom sides, facilitating installation and replacement.

To achieve these and other objects of the present invention, a wall socket mounted solid fragrance aroma diffuser comprises a bottom housing, an electrical plug assembly, an air delivery device, an air bearing seat and a plurality of breathable fragrance capsules. The bottom housing comprises an accommodation chamber, an open port and a mounting unit. The internal space of ther bottom housing defines the accommodation chamber. The open port is located on a top side of the bottom housing and disposed in communication with the accommodation chamber. The mounting unit is located at one lateral side of the bottom housing. The electrical plug assembly is mounted in between the accommodation chamber and the mounting unit of the bottom housing. The air delivery device is mounted inside the accommodation chamber of the bottom housing and electrically coupled to the electrical plug assembly and adapted for creating a flow of air. The air bearing seat is mounted in the open port at the top side of the bottom housing, comprising a seat mouth, a seat chamber and an air delivery hole. The seat mouth is located on a top side of the air bearing seat. The seat chamber extends downwardly from the seat mouth to the air delivery hole. The air delivery hole is disposed in communication with the accommodation chamber of the bottom housing. The breathable fragrance capsules each hold therein a solid fragrance material and are placed in the seat chamber in a stack. The solid fragrance material of each breathable fragrance capsule has open spaces therein for the passing of the flow of air being created by the air delivery device. Each breathable fragrance capsule comprises a first venting structure located on top side thereof and a second venting structure located on an opposing bottom side thereof.

Further, the accommodation chamber is not a completely enclosed space, it allows the air delivery device to draw outside air in. In some embodiments, an air inlet is located on one side, namely, the bottom side of the bottom housing. The air inlet further assists the air delivery device to draw outside air in.

In application, the wall socket mounted solid fragrance aroma diffuser does not need to use an electrical heater to heat the solid fragrance material or an oscillator to oscillate the fluid fragrance into a mist of fluid droplets. The breathable fragrance capsule has air vents in the opposing top and bottom sides so that the breathable fragrance capsule can be placed in the seat chamber on either of the top and bottom sides for diffusing a pleasant smell. The wall socket mounted solid fragrance aroma diffuser uses the air bearing seat to work with the air delivery device and the breathable fragrance capsule. In operation, the air delivery device keeps drawing outside air in so that the intake flow of air flows through the air delivery hole of the air bearing seat into the second venting structure or first venting structure of the breathable fragrance capsule to agitate the solid fragrance material in the breathable fragrance capsule and then carries the pleasant smell of the breathable fragrance capsule out of the breathable fragrance capsule to the outside open space via the first venting structure or second venting structure of the breathable fragrance capsule. The fragrant smell is not easily be diffused from the solid fragrance material by the solid fragrance material itself. By means of continuously delivering a flow of air through the first venting structure and second venting structure of the breathable fragrance capsule, the fragrant smell of the solid fragrance material in the breathable fragrance capsule is effectively diffused into the outside open space. Further, the user can conveniently take the used up breathable fragrance capsules out of the accommodation chamber and then place new or different smell of breathable fragrance capsules in the accommodation chamber without considering the upward or downward installation direction of breathable fragrance capsules. Therefore, the wall socket mounted solid fragrance aroma diffuser of the present invention is convenient and safe in use.

DETAILED DESCRIPTION OF THE PREFERRED EMBODIMENT

Referring to FIGS. 1-5, a wall socket mounted solid fragrance aroma diffuser in accordance with a first embodiment of the present invention is shown. The wall socket mounted solid fragrance aroma diffuser comprises a bottom housing 1, an electrical plug assembly 3, an air delivery device 5, and an air bearing seat 7. The bottom housing 1 comprises an accommodation chamber 11, an open port 13 and a mounting unit 15. The interior space of the bottom housing 1 defines the accommodation chamber 11. The open port 13 is located on the top side of the bottom housing 1 and disposed in communication with the accommodation chamber 11. The mounting unit 15 is located at one side of the bottom housing 1. The electrical plug assembly 3 is mounted in between the accommodation chamber 11 and mounting unit 15 of the bottom housing 1. The air delivery device 5 is mounted in the accommodation chamber 11 of the bottom housing 1 and electrically coupled to the electrical plug assembly 3. The air bearing seat 7 mounted in the open port 13 at the top side of the bottom housing 1, comprising a seat mouth 70, a seat chamber 72, and an air delivery hole 74. The seat mouth 70 is formed in the top side of the air bearing seat 7. The seat chamber 72 extends downwardly from the seat mouth 70 to the air delivery hole 74. The air delivery hole 74 is formed in the bottom side of the seat mouth 70.

The wall socket mounted solid fragrance aroma diffuser further comprises a breathable fragrance capsule 8 mounted in a bottom side inside the seat chamber 72. The breathable fragrance capsule 8 holds therein a solid fragrance substance, comprising a first venting structure 81 at a top side thereof and a second venting structure 83 at an opposing bottom side thereof.

The accommodation chamber 11 is not a completely enclosed space, it allows the air delivery device 5 to draw outside air in. In some embodiments, an air inlet 17 is located on one side, namely, the bottom side of the bottom housing 1. The air inlet 17 further assists the air delivery device 5 to draw outside air in. Further, the air delivery device 5 can be a fan, a pump or a pneumatic bottle. In the present preferred embodiment, a fan is used for the advantage of optimal air output effect and high safety. Those skilled in the art will be able to replace the fan function with other air delivery devices such as pumps or air pressure bottles.

The wall socket mounted solid fragrance aroma diffuser does not need to use an electrical heater to heat the solid fragrance material or an oscillator to oscillate the fluid fragrance into a mist of fluid droplets. The breathable fragrance capsule 8 has air vents in the opposing top and bottom sides. The breathable fragrance capsule 8 can be placed in the seat chamber 72 on either of the top and bottom sides for diffusing a pleasant smell. The wall socket mounted solid fragrance aroma diffuser uses the air bearing seat 7 to work with the air delivery device 5 and the breathable fragrance capsule 8. In operation, the air delivery device 5 keeps drawing outside air in so that the intake flow of air flows through the air delivery hole 74 of the air bearing seat 7 into the second venting structure 83 or first venting structure 81 of the breathable fragrance capsule 8 to agitate the solid fragrance material in the breathable fragrance capsule 8 and then carries the pleasant smell of the breathable fragrance capsule 8 out of the breathable fragrance capsule 8 to the outside open space via the first venting structure 81 or second venting structure 83 of the breathable fragrance capsule 8. The fragrant smell is not easily be diffused from the solid fragrance material by the solid fragrance material itself. By means of continuously delivering a flow of air through the first venting structure 81 and second venting structure 83 of the breathable fragrance capsule 8, the fragrant smell of the solid fragrance material in the breathable fragrance capsule 8 is effectively diffused into the outside open space.

When the solid fragrance material in the breathable fragrance capsule 8 is exhausted, the breathable fragrance capsule 8 can be conveniently taken out of the accommodation chamber 11 for replacement, and a new breathable fragrance capsule 8, or a different smell of breathable fragrance capsule 8 can be placed in the accommodation chamber 11 for use. Thus, the user can conveniently and rapidly replace the breathable fragrance capsule 8 to enjoy the atmosphere of aromatic air or to relax the odor in the space.

Referring to FIGS. 2, 4 and 5 again, the breathable fragrance capsule 8 further comprises a third venting structure 85. The third venting structure 85 is formed around the breathable fragrance capsule 8 between the first venting structure 81 and the second venting structure 83. When a continuous flow of air flows through the first venting structure 81 and second venting structure 83 of the breathable fragrance capsule 8, the fragrance molecules of the solid fragrance material can also be carried through the open spaces in the third venting structure 85, enhancing fragrance diffusion.

Figure 6:
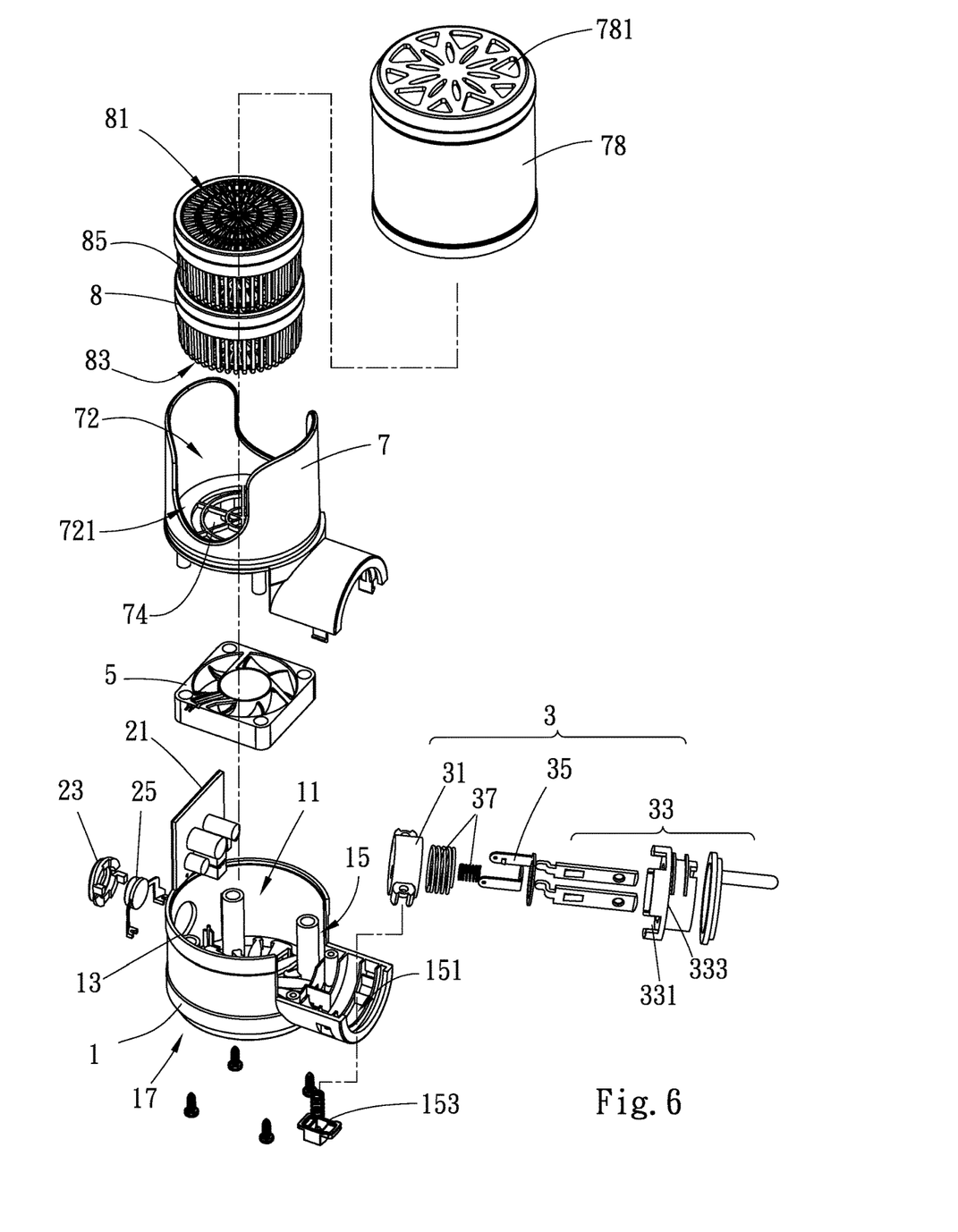
FIG. 6 is an exploded view of a wall socket mounted solid fragrance aroma diffuser in accordance with a second embodiment of the present invention.
Figure 7:
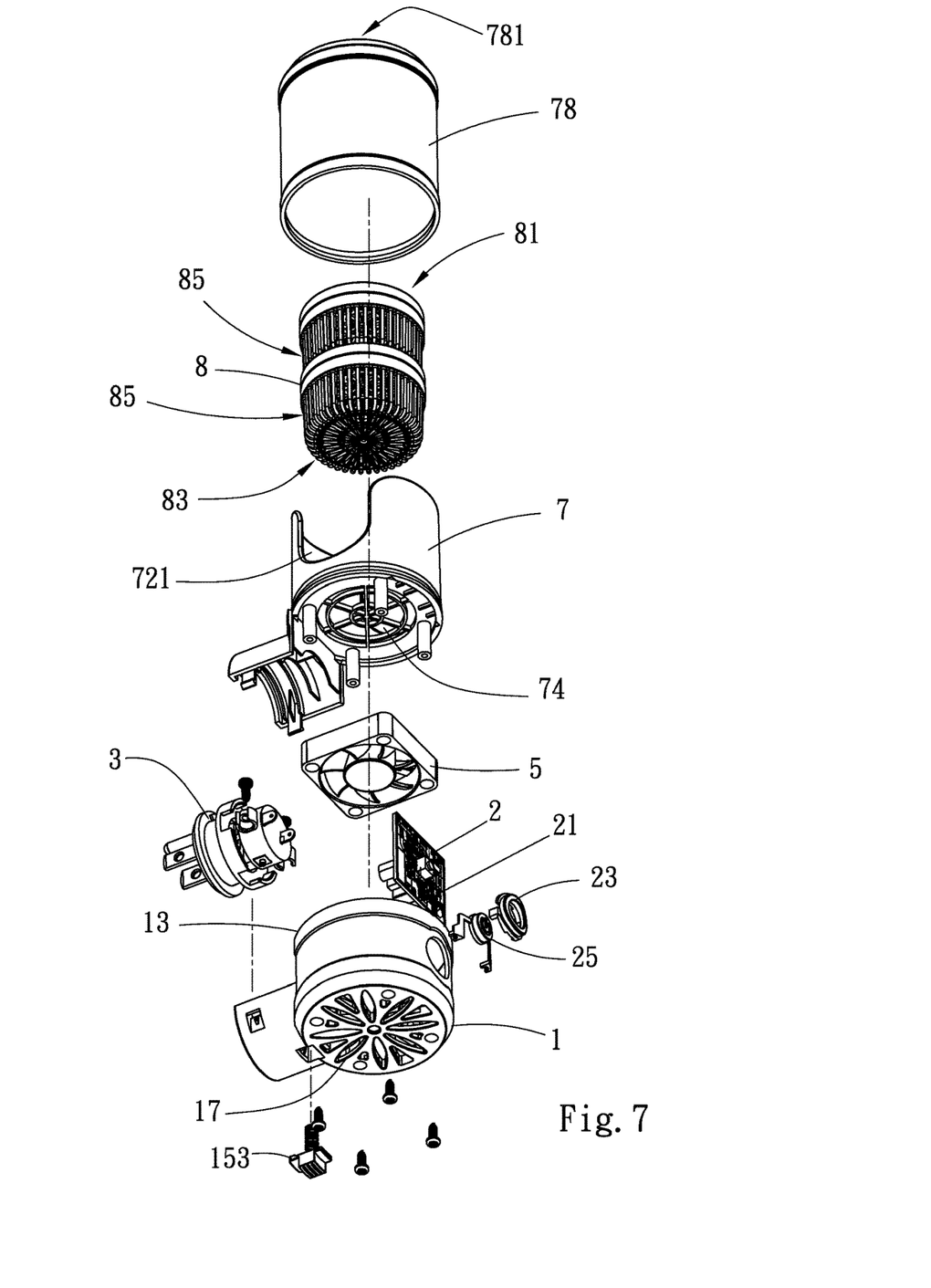
FIG. 7 is another exploded view of the wall socket mounted solid fragrance aroma diffuser in accordance with the second embodiment of the present invention.
Figure 8:
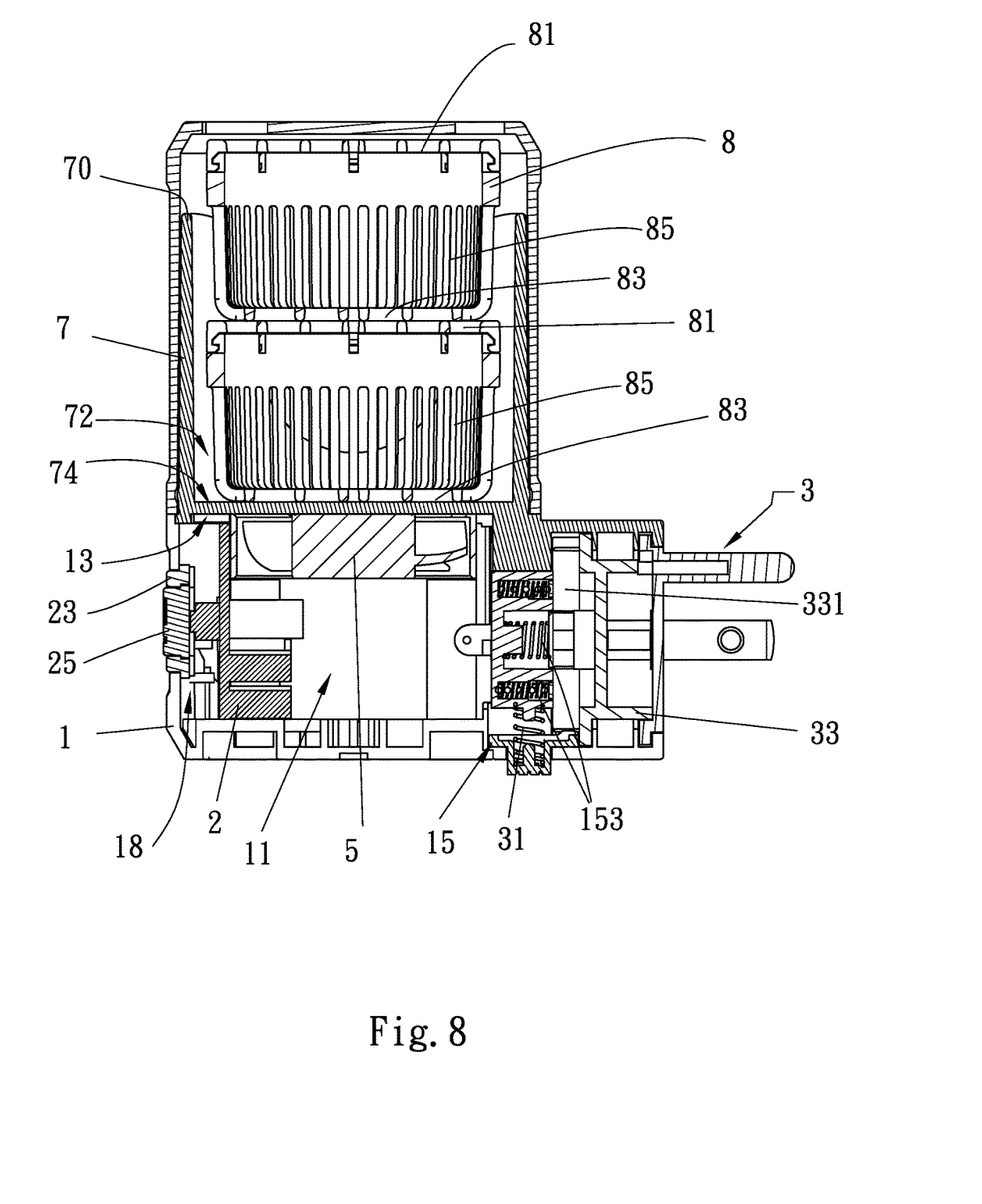
FIG. 8 is a sectional side view of the wall socket mounted solid fragrance aroma diffuser in accordance with the second embodiment of the present invention.

Referring to FIGS. 6-8, a wall socket mounted solid fragrance aroma diffuser in accordance with a first embodiment of the present invention is shown. The wall socket mounted solid fragrance aroma diffuser comprises a bottom housing 1, an electrical plug assembly 3, an air delivery device 5, an air bearing seat 7 and a plurality of breathable fragrance capsules 8. The bottom housing 1 comprises an accommodation chamber 11, an open port 13, a mounting unit 15 and an air inlet 17. The interior space of the bottom housing 1 defines the accommodation chamber 11. The open port 13 is located on the top side of the bottom housing 1 and disposed in communication with the accommodation chamber 11. The mounting unit 15 is located at one side of the bottom housing 1. The air inlet 17 is located on one side, namely, the bottom side of the bottom housing 1. The electrical plug assembly 3 is mounted in between the accommodation chamber 11 and mounting unit 15 of the bottom housing 1. The air delivery device 5 is mounted in the accommodation chamber 11 of the bottom housing 1 and electrically coupled to the electrical plug assembly 3. The air bearing seat 7 mounted in the open port 13 at the top side of the bottom housing 1, comprising a seat mouth 70, a seat chamber 72, and an air delivery hole 74. The seat mouth 70 is formed in the top side of the air bearing seat 7. The seat chamber 72 extends downwardly from the seat mouth 70 to the air delivery hole 74. The air delivery hole 74 is formed in the bottom side of the seat mouth 70. The breathable fragrance capsules 8 are arranged in a stack and mounted in the seat chamber 72. The breathable fragrance capsules 8 respectively hold therein a solid fragrance substance of a different fragrant smell, each comprising a first venting structure 81 at a top side thereof, a second venting structure 83 at an opposing bottom side thereof and a third venting structure 85 around the periphery thereof. Preferably, the breathable fragrance capsules 8 hold therein different smell solid fragrance materials. Fragrance adjusters can design a variety of cocktail style fragrance recipes in the individual breathable fragrance capsules 8. Subject to the structural design and the functioning of the air delivery device 5 to deliver a flow of air through the stack of breathable fragrance capsules 8, a combination of pleasant smells is generated and diffused into the outside open space. In this embodiment, two breathable fragrance capsules 8 are used and mounted in the seat chamber 72 in a stack. However, this example is not a limitation three or more than three breathable fragrance capsules 8 can be used and mounted in the seat chamber 72 in a stack.

Figure 1:
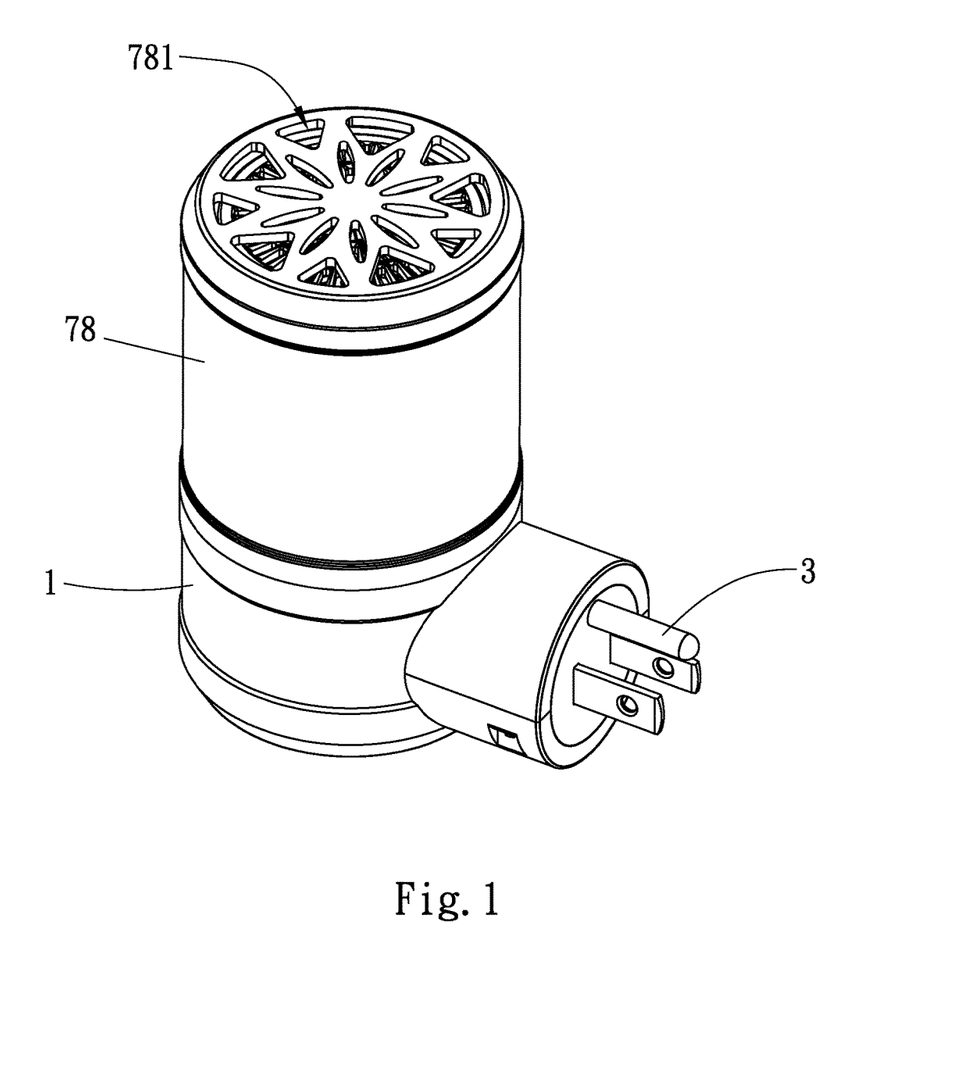
FIG. 1 is an oblique top elevation of a wall socket mounted solid fragrance aroma diffuser in accordance with a first embodiment of the present invention.
Figure 2:
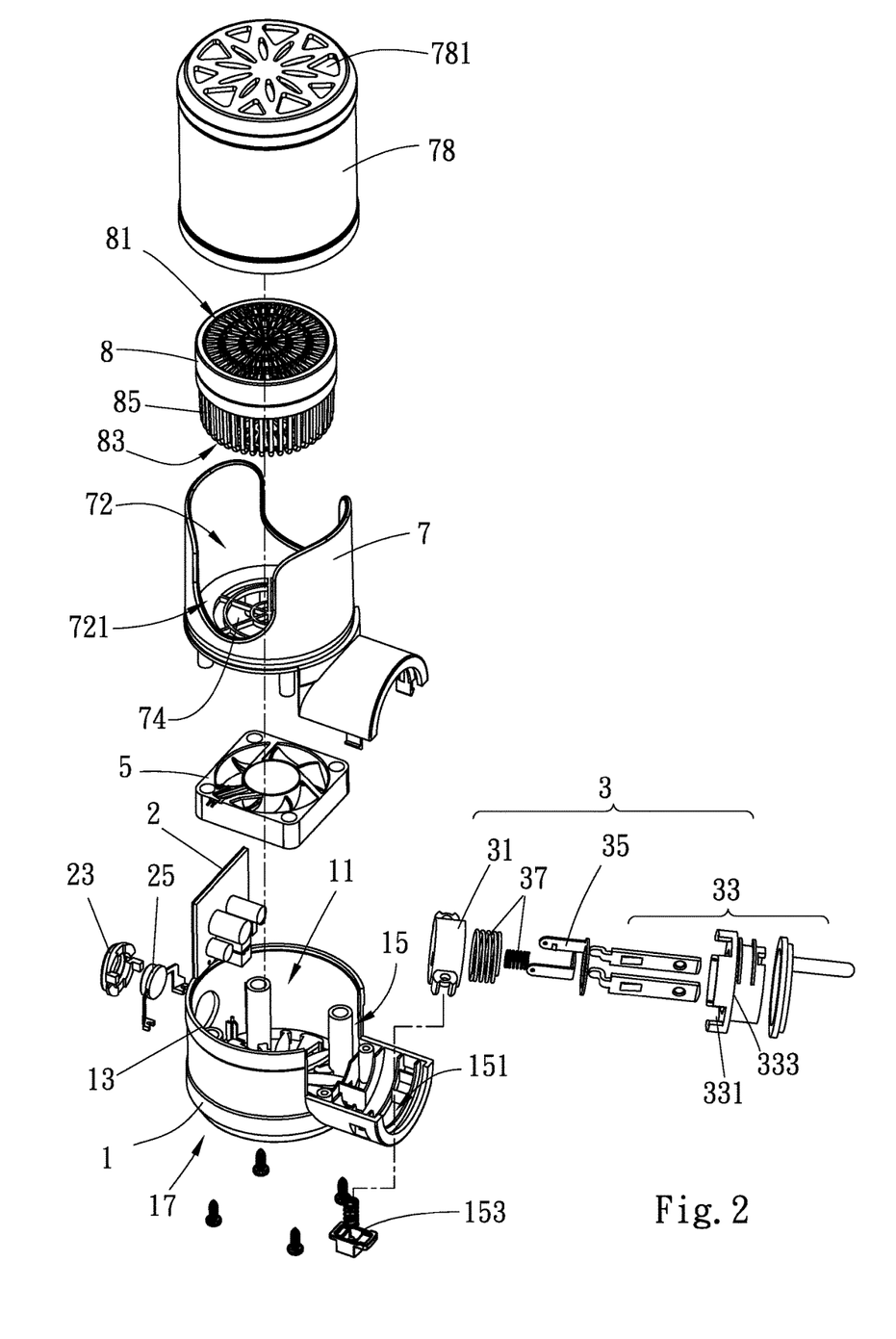
FIG. 2 is an exploded view of the wall socket mounted solid fragrance aroma diffuser in accordance with the first embodiment of the present invention.
Figure 3:
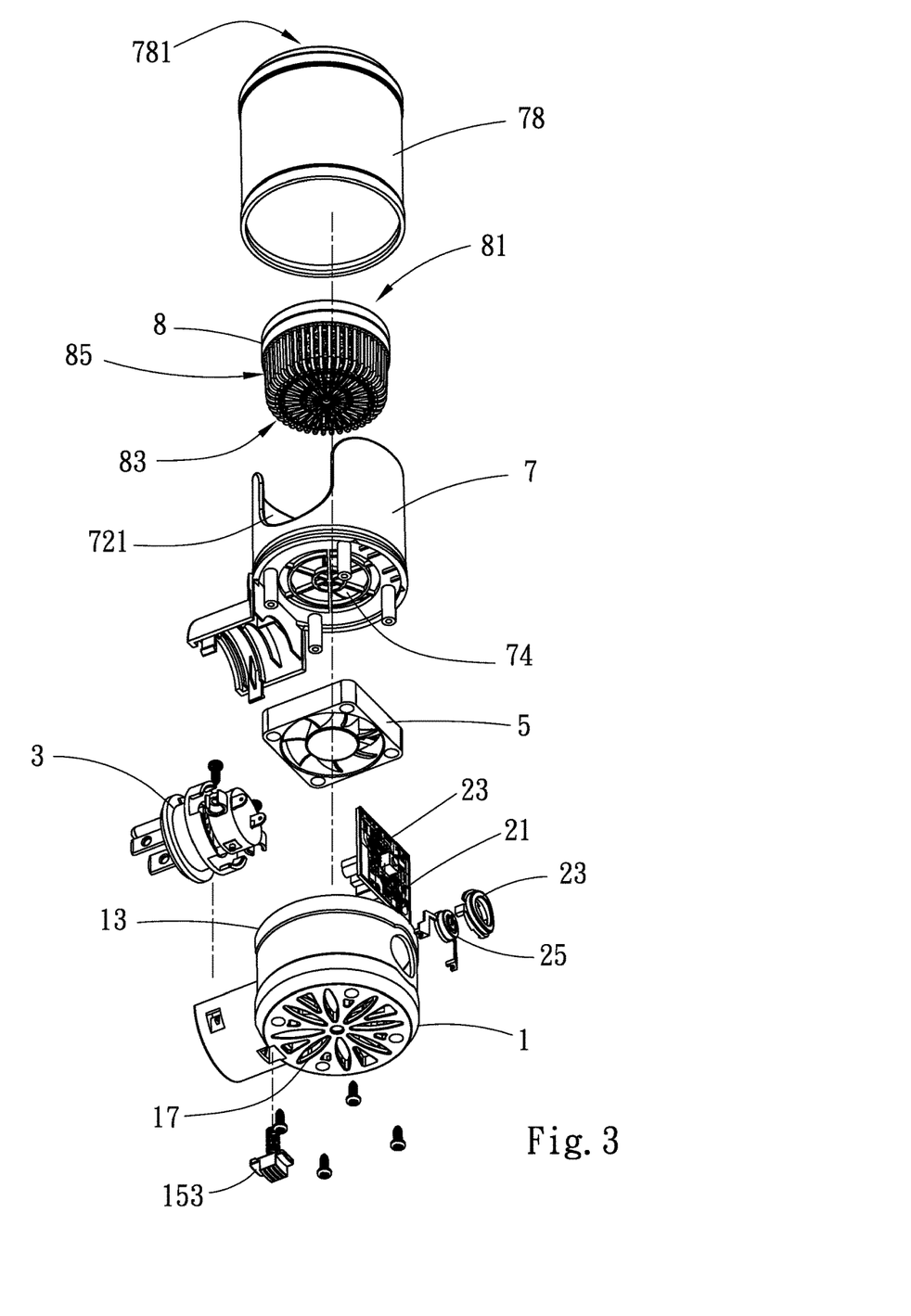
FIG. 3 is another exploded view of the wall socket mounted solid fragrance aroma diffuser in accordance with the first embodiment of the present invention.
Figure 4:
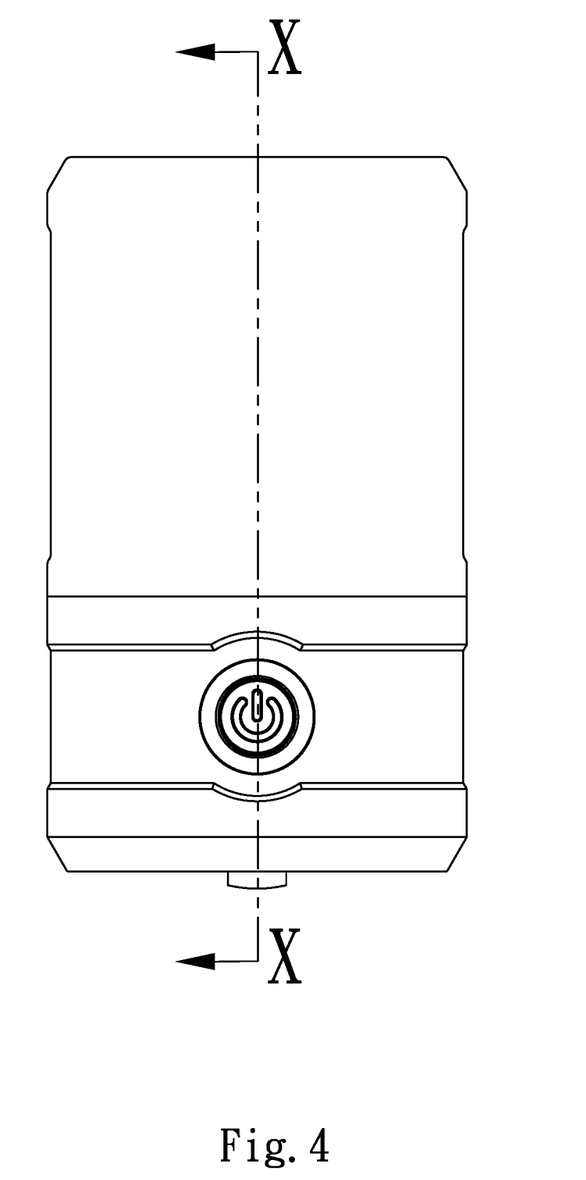
FIG. 4 is a side plain view of the wall socket mounted solid fragrance aroma diffuser in accordance with the first embodiment of the present invention.
Figure 5:
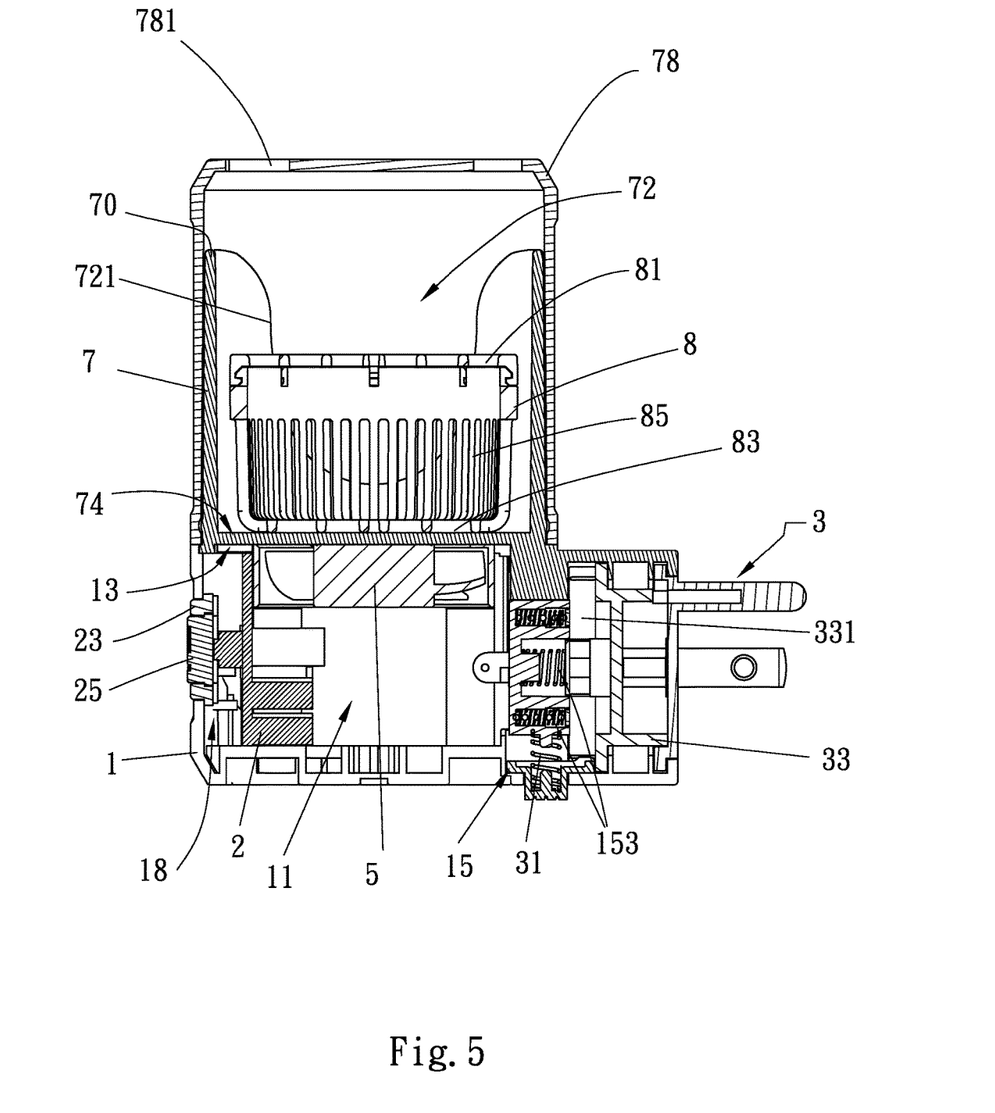
FIG. 5 is a sectional view taken along line X-X of FIG. 4.

Referring to FIGS. 1, 6 and 8, the air bearing seat 7 further comprises a ventilation hood 78. The ventilation hood 78 comprises an air outlet 781 formed on the top side thereof. The opposing bottom side of the ventilation hood 78 is an open side. By means of the bottom open side, the ventilation hood 78 is capped on the air bearing seat 7 to cover the breathable fragrance capsules 8. When the air delivery device 5 is turned on to deliver a flow of air through the seat chamber 72, the stack of breathable fragrance capsules 8 and the seat mouth 70, the flow of air carries the pleasant smell of the solid fragrance materials in the breathable fragrance capsules 8 through the air outlet 781 to the outside open space, and thus the aroma of the solid fragrance materials is diffused into the outside open space.

Referring to FIGS. 1, 6 and 8, the electrical plug assembly 3 is a rotary plug structure comprising a pressure ring 31, a rotary plug 33, a conducting ring 35 and a spring set 37. The rotary plug 33 comprises a plug body 333. The plug body 333 has a plurality of angularly spaced retaining notches 331. The pressure ring 31, the spring set 37, the conducting ring 35 and the rotary plug 33 are assembled inside the mounting unit 15, allowing the conducting contact blades of the rotary plug 33 to expose to the outside of the mounting unit 15. The rotary plug 33 is rotatably and electrically coupled to the conducting ring 35. The mounting unit 15 comprises an opening 151, and a spring-loaded button 153 mounted in the opening 151. The retaining notches 331 are selectively shifted into alignment with the spring-loaded button 153 so that the spring-loaded button 153 can be detachably engaged into one of the retaining notches 331 to lock the rotary plug 33. When the spring-loaded button 153 is pressed and kept in the pressed condition, the retaining notches 331 of the rotary plug 33 are disengaged from the spring-loaded button 153, thus, the rotary plug 33 is unlocked and can be rotated relative to the bottom housing 1 to the desired angular position where another retaining notch 331 is shifted into alignment with the spring-loaded button 153. When the user releases the pressure from the spring-loaded button 153 at this time, the rotary plug 33 is locked in the adjusted angular position. The retaining notches 331 can be located at, for example, 90° angle, 180° angle and 270° angle.

The aforesaid solid fragrance material can be an aromatic wax block, a porous ceramic block, porous plastic sheet, porous paper block or porous wooden block filled with a fragrance substance, or a fragrance substance loaded meteorite. The fragrance substance can be made in powder, particles or chips of irregular shapes. The solid fragrance material has open spaces therein so that an airflow can flow through the open spaces in the solid fragrance material to carry the pleasant smell out of the breathable fragrance capsules 8 into the outside open air.

Referring to FIGS. 1, 6 and 8, the breathable fragrance capsules 8 have a cylindrical shape. The first venting structure 81 or the second venting structure 83 can be a ventilation grille that defines therein a plurality of transversely and longitudinally aligned air holes, or a radial ventilation grille with radially aligned air holes for guiding air into the inside of the breathable fragrance capsules 8 to produce a better aromatic effect.

Referring to FIGS. 1, 6 and 8, two recessed portions 721 are formed on the peripheral wall of the seat chamber 72 at two opposite sides. Through either one of the recessed portions 721, the user can conveniently place the breathable fragrance capsules 8 in the seat chamber 72 or taken the breathable fragrance capsules 8 out of the seat chamber 72 for a replacement.

Referring to FIG. 1 and FIGS. 6-8, the wall socket mounted solid fragrance aroma diffuser further comprises a circuit board 2, a light-emitting device 21, a light guide ring 23 and a press button 25. The light-emitting device 21 and the circuit board 2 are electrically coupled together. The circuit board 2 is electrically coupled with the electrical plug assembly 3 and the air delivery device 5. The circuit board 2 and the light-emitting device 21 are mounted in the accommodation chamber 11 of the bottom housing 1. The light guide ring 23 is mounted in a hole on the peripheral wall of the bottom housing 1. The press button 25 is mounted within the light guide ring 23, and operable to switch on/off a power switch of the circuit board 2. When pressed the press button 25 to switch on the circuit board 2, the circuit board 2 drives the air delivery device and the light-emitting device 21 to operate, causing the light-emitting device 21 to emit a color light. The light guide ring 23 guides the color light emitted by the light-emitting device 21 to the outside of the bottom housing 1, creating a dimming effect and giving a visual signal indicative of the operation of the circuit board 2. Further, the light-emitting device 21 can be a light-emitting diode (LED) or incandescent lamp bulb.

Although particular embodiments of the present invention have been described in detail for purposes of illustration, various modifications and enhancements may be made without departing from the spirit and scope of the invention. Accordingly, the invention is not to be limited except as by the appended claims.

What the invention claimed is:

1. A wall socket mounted solid fragrance aroma diffuser, comprising:
   a bottom housing comprising an accommodation chamber, an open port and a mounting unit, the internal space of said bottom housing defining said accommodation chamber, said open port being located on a top side of said bottom housing and disposed in communication with said accommodation chamber, said mounting unit being located at one lateral side of said bottom housing;

an electrical plug assembly mounted in between said accommodation chamber and said mounting unit of said bottom housing;

an air delivery device mounted inside said accommodation chamber of said bottom housing and electrically coupled to said electrical plug assembly and adapted for creating a flow of air;

an air bearing seat mounted in said open port at the top side of said bottom housing, said air bearing seat comprising a seat mouth, a seat chamber and an air delivery hole, said seat mouth being located on a top side of said air bearing seat, said seat chamber being downwardly extended from said seat mouth to said air delivery hole, said air delivery hole being disposed in communication with said accommodation chamber of said bottom housing; and at least one breathable fragrance capsule holding therein a solid fragrance material and placed in said seat chamber, said solid fragrance material having open spaces therein for the passing of the flow of air being created by said air delivery device, each said breathable fragrance capsule comprising a first venting structure located on top side thereof and a second venting structure located on an opposing bottom side thereof.

2. The wall socket mounted solid fragrance aroma diffuser as claimed in claim 1, wherein each said breathable fragrance capsule further comprises a third venting structure located around the periphery thereof between said first venting structure and said second venting structure.

3. The wall socket mounted solid fragrance aroma diffuser as claimed in claim 2, wherein each said breathable fragrance capsule has a cylindrical shape; said first venting structure and said second venting structure being respectively formed of a radial ventilation grille having a plurality of radially aligned air vents.

4. The wall socket mounted solid fragrance aroma diffuser as claimed in claim 3, wherein a plurality of said breathable fragrance capsules are arranged in said seat chamber in a stack, and the solid fragrance materials in the plurality of said breathable fragrance capsules contain different aromas.

5. The wall socket mounted solid fragrance aroma diffuser as claimed in claim 1, wherein said bottom housing further comprises two recessed portions located on the periphery thereof at two opposite lateral sides relative to said seat chamber.

6. The wall socket mounted solid fragrance aroma diffuser as claimed in claim 1, further comprising a ventilation hood detachably capped on said air bearing seat to cover said at least one breathable fragrance capsule, said ventilation hood comprising an air outlet located on a top side thereof.

7. The wall socket mounted solid fragrance aroma diffuser as claimed in claim 1, wherein said electrical plug assembly is a rotary plug structure comprising a pressure ring, a rotary plug, a conducting ring and a spring set, said rotary plug comprising a plug body, said plug body having a plurality of angularly spaced retaining notches, said pressure ring, said spring set, said conducting ring and said rotary plug being assembled inside said mounting unit for allowing conducting contact blades of said rotary plug to expose to the outside of said mounting unit, said rotary plug being rotatably and electrically coupled to said conducting ring; said mounting unit comprising an opening and a spring-loaded button mounted in said opening, said retaining notches being selectively shifted into alignment with said spring-loaded button upon rotation of said electrical plug assembly in said mounting unit so that said spring-loaded button is detachably engaged into one of said retaining notches to lock said rotary plug to said mounting unit.

8. A wall socket mounted solid fragrance aroma diffuser, comprising:

a bottom housing comprising an accommodation chamber, an open port and a mounting unit, the internal space of said bottom housing defining said accommodation chamber, said open port being located on a top side of said bottom housing and disposed in communication with said accommodation chamber, said mounting unit being located at one lateral side of said bottom housing;

an electrical plug assembly mounted in between said accommodation chamber and said mounting unit of said bottom housing;

an air delivery device mounted inside said accommodation chamber of said bottom housing and electrically coupled to said electrical plug assembly and adapted for creating a flow of air; and an air bearing seat mounted in said open port at the top side of said bottom housing, said air bearing seat comprising a seat mouth, a seat chamber and an air delivery hole, said seat mouth being located on a top side of said air bearing seat, said seat chamber being downwardly extended from said seat mouth to said air delivery hole, said air delivery hole being disposed in communication with said accommodation chamber of said bottom housing.

9. The wall socket mounted solid fragrance aroma diffuser as claimed in claim 8, further comprising at least one breathable fragrance capsule placed in said seat chamber, each said breathable fragrance capsule holding therein a solid fragrance material, said solid fragrance material having open spaces therein for the passing of the flow of air being created by said air delivery device, each said breathable fragrance capsule comprising a first venting structure located on top side thereof and a second venting structure located on an opposing bottom side thereof.

10. The wall socket mounted solid fragrance aroma diffuser as claimed in claim 9, wherein each said breathable fragrance capsule further comprises a third venting structure located around the periphery thereof between said first venting structure and said second venting structure.

11. The wall socket mounted solid fragrance aroma diffuser as claimed in claim 10, wherein each breathable fragrance capsule has a cylindrical shape; said first venting structure and said second venting structure being respectively formed of a radial ventilation grille having a plurality of radially aligned air vents.

12. The wall socket mounted solid fragrance aroma diffuser as claimed in claim 11, wherein a plurality of said breathable fragrance capsules are arranged in said seat chamber in a stack, and the solid fragrance materials in the plurality of said breathable fragrance capsules contain different aromas.

13. The wall socket mounted solid fragrance aroma diffuser as claimed in claim 8, wherein said bottom housing further comprises two recessed portions located on the periphery thereof at two opposite lateral sides relative to said seat chamber.

14. The wall socket mounted solid fragrance aroma diffuser as claimed in claim 8, further comprising a ventilation hood detachably capped on said air bearing seat to cover said at least one breathable fragrance capsule, said ventilation hood comprising an air outlet located on a top side thereof.

15. The wall socket mounted solid fragrance aroma diffuser as claimed in claim 8, wherein said electrical plug assembly is a rotary plug structure comprising a pressure ring, a rotary plug, a conducting ring and a spring set, said rotary plug comprising a plug body, said plug body having a plurality of angularly spaced retaining notches, said pressure ring, said spring set, said conducting ring and said rotary plug being assembled inside said mounting unit for allowing conducting contact blades of said rotary plug to expose to the outside of said mounting unit, said rotary plug being rotatably and electrically coupled to said conducting ring; said mounting unit comprising an opening and a spring-loaded button mounted in said opening, said retaining notches being selectively shifted into alignment with said spring-loaded button upon rotation of said electrical plug assembly in said mounting unit so that said spring-loaded button is detachably engaged into one of said retaining notches to lock said rotary plug to said mounting unit.

\* \* \* \* \*